(12) United States Patent
Patterson et al.

(10) Patent No.: US 11,780,800 B1
(45) Date of Patent: Oct. 10, 2023

(54) FLUORINATED PHENYLAMINO COMPOUNDS AND PHARMACEUTICAL COMPOSITIONS

(71) Applicant: SpringWorks Therapeutics Inc., Stamford, CT (US)

(72) Inventors: Kristin Patterson, Stamford, CT (US); Piero L Ruggiero, Stamford, CT (US)

(73) Assignee: SPRINGWORKS THERAPEUTICS, INC., Stamford, CT (US)

( * ) Notice: Subject to any disclaimer, the term of this patent is extended or adjusted under 35 U.S.C. 154(b) by 0 days.

(21) Appl. No.: 18/185,180

(22) Filed: Mar. 16, 2023

Related U.S. Application Data

(60) Provisional application No. 63/321,043, filed on Mar. 17, 2022.

(51) Int. Cl.
*C07C 211/55* (2006.01)
*A61K 31/166* (2006.01)
*C07C 291/04* (2006.01)

(52) U.S. Cl.
CPC .......... *C07C 211/55* (2013.01); *A61K 31/166* (2013.01); *C07C 291/04* (2013.01)

(58) Field of Classification Search
CPC .......................... C07C 211/55; A61K 31/166
See application file for complete search history.

(56) References Cited

U.S. PATENT DOCUMENTS

| | | | |
|---|---|---|---|
| 6,960,614 B2 | 11/2005 | Barrett et al. |
| 7,060,856 B2 | 6/2006 | Macikenas et al. |
| 11,427,534 B1 | 8/2022 | Patterson et al. |
| 11,453,641 B2 | 9/2022 | Irdam |
| 11,571,402 B2 | 2/2023 | Patterson et al. |
| 2011/0263558 A1 | 10/2011 | Aay et al. |

FOREIGN PATENT DOCUMENTS

WO 2020106303 A1 5/2020

OTHER PUBLICATIONS

International Search Report issued in PCT/US2023/064569 dated Aug. 23, 2023.

Klesse, et al., The Use of MEK Inhibitors in Neurofibromatosis Type 1-associated Tumors and Management of Toxicities in Journal in the Oncologist, 2020, 25:e1109-1116 Abstract.

*Primary Examiner* — James D. Anderson
(74) *Attorney, Agent, or Firm* — Blank Rome LLP

(57) ABSTRACT

The present disclosure relates to fluorinated phenylamino compounds, their pharmaceutical compositions, and methods for treating one or more tumors or cancers selected from the group consisting of plexiform neurofibromas (PN), plexiform neurofibromas associated with neurofibromatosis type 1 (NF1-PN), cutaneous neurofibromas (cNF), pancreatic ductal adenocarcinoma (PDAC), high grade glioma (HGG), low grade ovarian cancer, tuberous sclerosis (TSC), Langerhans cell histiocytosis (LCH), brain cancer, and a cancer that has metastasized to a patient's brain, comprising administering to a patient in need thereof, those pharmaceutical compositions.

18 Claims, No Drawings

FLUORINATED PHENYLAMINO COMPOUNDS AND PHARMACEUTICAL COMPOSITIONS

This application claims the benefit of U.S. Provisional Application No. 63/321,043, filed Mar. 17, 2022, which is hereby incorporated by reference.

FIELD OF THE INVENTION

The present disclosure relates to fluorinated phenylamino compounds, their pharmaceutical compositions, and methods for treating one or more tumors or cancers selected from the group consisting of plexiform neurofibromas (PN), plexiform neurofibromas associated with neurofibromatosis type 1 (NF1-PN), cutaneous neurofibromas (cNF), pancreatic ductal adenocarcinoma (PDAC), high grade glioma (HGG), low grade ovarian cancer, tuberous sclerosis (TSC), Langerhans cell histiocytosis (LCH), brain cancer, and a cancer that has metastasized to a patient's brain, comprising administering to a patient in need thereof, those pharmaceutical compositions.

BACKGROUND

Because objective responses are rarely complete and disease recurrence after completion of therapy is common in the tumors and cancers listed above, there is a need to find a better treatment.

BRIEF SUMMARY OF THE INVENTION

A compound which is

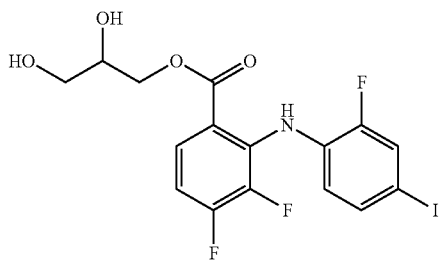

or a pharmaceutically acceptable salt thereof is provided herein.

A compound which is

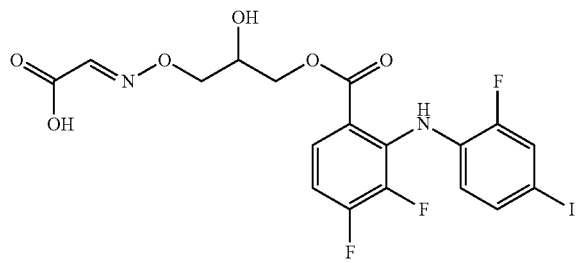 [SMILES: O=C(O)/C=N/OCC(O)COC(=O)c1ccc(F)c(F)c1Nc1ccc(I)cc1F]

or a pharmaceutically acceptable salt thereof is provided herein.

A compound which is

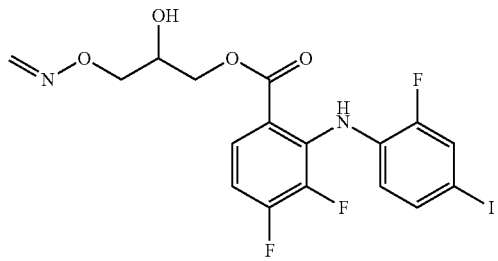 [SMILES: C=NOCC(O)COC(=O)c1ccc(F)c(F)c1Nc1ccc(I)cc1F]

or a pharmaceutically acceptable salt thereof is provided herein.

In one embodiment, the compound is (R)-3,4-difluoro-2-(2-fluoro-4-iodo-phenylamino)benzoic acid 2,3-dihydroxypropyl ester or a pharmaceutically acceptable salt thereof (e.g., (R)-3,4-difluoro-2-(2-fluoro-4-iodo-phenylamino) benzoic acid 2,3-dihydroxypropyl ester). In another embodiment, the compound is (S)-3,4-difluoro-2-(2-fluoro-4-iodo-phenylamino)benzoic acid 3-[1-carboxy-meth-(E)-ylideneaminooxy]-2-hydroxypropyl ester or a pharmaceutically acceptable salt thereof (e.g., (S)-3,4-difluoro-2-(2-fluoro-4-iodo-phenylamino)benzoic acid 3-[1-carboxy-meth-(E)-ylideneaminooxy]-2-hydroxypropyl ester). In yet another embodiment the compound is (S)-3, 4-difluoro-2-(2-fluoro-4-iodo-phenylamino)-benzoic acid 2-hydroxy-3-methyleneaminooxy-propyl ester or a pharmaceutically acceptable salt thereof (e.g., (S)-3,4-difluoro-2-(2-fluoro-4-iodo-phenylamino)-benzoic acid 2-hydroxy-3-methyleneaminooxy-propyl ester).

Pharmaceutical compositions comprising a compound selected from the group consisting of: 3,4-difluoro-2-(2-fluoro-4-iodo-phenylamino)benzoic acid 2,3-dihydroxypropyl ester; 3,4-difluoro-2-(2-fluoro-4-iodo-phenylamino) benzoic acid 3-[1-carboxy-meth-(E)-ylideneaminooxy]-2-hydroxypropyl ester; 3,4-difluoro-2-(2-fluoro-4-iodo-phenylamino)-benzoic acid 2-hydroxy-3-methyleneaminooxy-propyl ester; and pharmaceutically acceptable salts thereof, are provided herein.

Pharmaceutical compositions comprising a compound which is

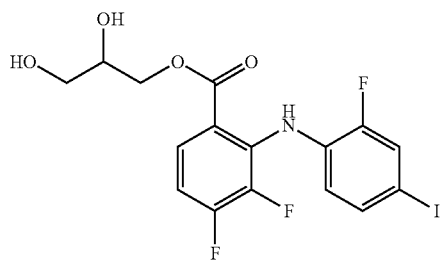 [SMILES: O=C(OCC(O)CO)c1ccc(F)c(F)c1Nc1ccc(I)cc1F]

or a pharmaceutically acceptable salt thereof are provided herein. In one embodiment, the pharmaceutical composition comprises (R)-3,4-difluoro-2-(2-fluoro-4-iodo-phenylamino)benzoic acid 2,3-dihydroxypropyl ester or a pharmaceutically acceptable salt thereof (e.g., (R)-3,4-difluoro-2-(2-fluoro-4-iodo-phenylamino)benzoic acid 2,3-dihydroxypropyl ester).

Pharmaceutical compositions comprising a compound which is

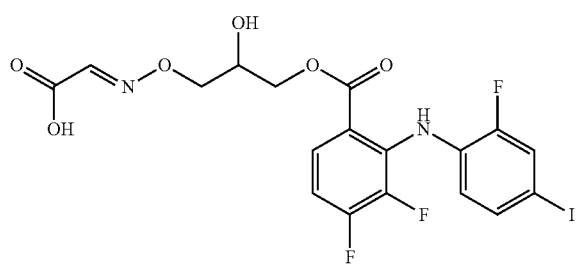 [SMILES: O=C(O)/C=N/OCC(O)COC(=O)c1ccc(F)c(F)c1Nc1ccc(I)cc1F]

or a pharmaceutically acceptable salt thereof are provided herein. In one embodiment, the pharmaceutical composition comprises (S)-3,4-difluoro-2-(2-fluoro-4-iodo-phenylamino)benzoic acid 3-[1-carboxy-meth-(E)-ylideneaminooxy]-2-hydroxypropyl ester or a pharmaceutically acceptable salt thereof (e.g., (S)-3,4-difluoro-2-(2-fluoro-4-iodo-phenylamino)benzoic acid 3-[1-carboxy-meth-(E)-ylideneaminooxy]-2-hydroxypropyl ester).

Pharmaceutical compositions comprising a compound which is

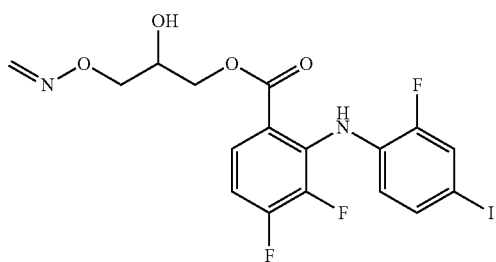 [SMILES: C=NOCC(O)COC(=O)c1ccc(F)c(F)c1Nc1ccc(I)cc1F]

or a pharmaceutically acceptable salt thereof are provided herein. In one embodiment, the pharmaceutical composition comprises (S)-3,4-difluoro-2-(2-fluoro-4-iodo-phenylamino)-benzoic acid 2-hydroxy-3-methyleneaminooxypropyl ester or a pharmaceutically acceptable salt thereof (e.g., (S)-3,4-difluoro-2-(2-fluoro-4-iodo-phenylamino)-benzoic acid 2-hydroxy-3-methyleneaminooxy-propyl ester).

The aforementioned pharmaceutical compositions may further include an additional MEK inhibitor selected from the group consisting of mirdametinib, binimetinib, cobimetinib, trametinib, and selumetinib, or a pharmaceutically acceptable salt thereof. In one embodiment, the pharmaceutical composition in any of the embodiments described herein further comprises mirdametinib.

Methods for treating one or more tumors or cancers selected from the group consisting of plexiform neurofibromas (PN), plexiform neurofibromas associated with neurofibromatosis type 1 (NF1-PN), cutaneous neurofibromas (cNF), pancreatic ductal adenocarcinoma (PDAC), high grade glioma (HGG), low grade ovarian cancer, tuberous sclerosis (TSC), Langerhans cell histiocytosis (LCH), brain cancer, and a cancer that has metastasized to a patient's brain, comprising administering to a patient in need thereof a pharmaceutical composition provided above.

One embodiment is a method for treating plexiform neurofibromas associated with neurofibromatosis type 1 (NF1-PN) in a patient in need thereof by administering to the patient a pharmaceutical composition as described herein. The pharmaceutical composition may be administered orally. Another embodiment is a method for treating NF1-PN in a patient in need thereof by orally administering to the patient an effective amount of one or more pharmaceutical compositions as described herein.

DETAILED DESCRIPTION OF THE INVENTION

I. Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "mirdametinib" refers to the single enantiomer N-((R)-2,3-dihydroxypropoxy)-3,4-difluoro-2-(2-fluoro-4-iodo-phenylamino)-benzamide.

The term "mg/m$^2$" refers to the dose in milligrams per m$^2$ body surface area of the patient.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for a tumor, according to the methods described herein if the patient shows one or more of the following: a reduction in the size of the tumor; relief of one or more symptoms associated with the specific tumor; a reduction in the volume of the tumor; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given tumor can be used to determine whether an effective amount of the active ingredient meets any of these particular endpoints (e.g., CR, PFS, PR).

In certain aspects, a subject is successfully "treated" for cancer, e.g., lung cancer or ovarian cancer, according to the methods described herein if the patient shows one or more of the following: a reduction in the number of or complete absence of cancer cells; relief of one or more symptoms associated with the specific cancer; reduced morbidity and mortality; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given cancer can be used to determine whether an effective amount of the active ingredient meets any of these particular endpoints (e.g., CR, PFS, PR).

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy*, 21st Edition, Lippincott Williams & Wilkins: Philadelphia, Pa., 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; Pharmaceutical Preformulation and Formulation, Gibson Ed., CRC Press LLC: Boca Raton, Fla., 2004 (incorporated herein by reference).

The term "pharmaceutically-acceptable salts" refers to the relatively non-toxic, inorganic and organic acid addition salts of Compound A or Compound B. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain aspects, the compounds of the present invention may contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

The terms "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

II. Compounds and Pharmaceutical Compositions

A compound which is

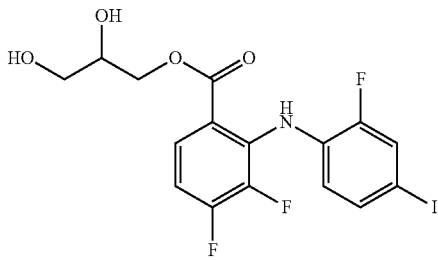 [SMILES: O=C(OCC(O)CO)c1ccc(F)c(F)c1Nc1ccc(I)cc1F]

or a pharmaceutically acceptable salt thereof is provided herein. In one embodiment, the compound is (R)-3,4-difluoro-2-(2-fluoro-4-iodo-phenylamino)benzoic acid 2,3-dihydroxypropyl ester or a pharmaceutically acceptable salt thereof (e.g., (R)-3,4-difluoro-2-(2-fluoro-4-iodo-phenylamino)benzoic acid 2,3-dihydroxypropyl ester).

A compound which is

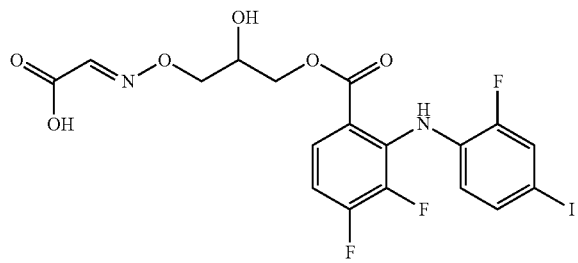 [SMILES: O=C(O)/C=N/OCC(O)COC(=O)c1ccc(F)c(F)c1Nc1ccc(I)cc1F]

or a pharmaceutically acceptable salt thereof is provided herein. In one embodiment, the compound is (S)-3,4-difluoro-2-(2-fluoro-4-iodo-phenylamino)benzoic acid 3-[1-carboxy-meth-(E)-ylideneaminooxy]-2-hydroxypropyl ester or a pharmaceutically acceptable salt thereof (e.g., (S)-3,4-difluoro-2-(2-fluoro-4-iodo-phenylamino)benzoic acid 3-[1-carboxy-meth-(E)-ylideneaminooxy]-2-hydroxypropyl ester).

A compound which is

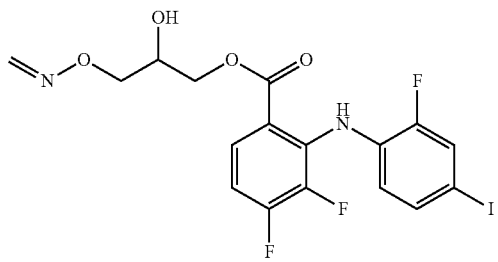 [SMILES: C=NOCC(O)COC(=O)c1ccc(F)c(F)c1Nc1ccc(I)cc1F]

or a pharmaceutically acceptable salt thereof is provided herein. In one embodiment the compound is (S)-3,4-difluoro-2-(2-fluoro-4-iodo-phenylamino)-benzoic acid 2-hydroxy-3-methyleneaminooxy-propyl ester or a pharmaceutically acceptable salt thereof (e.g., (S)-3,4-difluoro-2-(2-fluoro-4-iodo-phenylamino)-benzoic acid 2-hydroxy-3-methyleneaminooxy-propyl ester).

Pharmaceutical compositions comprising a compound selected from the group consisting of: 3,4-Difluoro-2-(2-fluoro-4-iodo-phenylamino)-benzoic acid 2,3-dihydroxypropyl ester; 3,4-Difluoro-2-(2-fluoro-4-iodo-phenylamino)-benzoic acid 3-[1-carboxy-meth-(E)-ylideneaminooxy]-2-hydroxy-propyl ester; 3,4-Difluoro-2-(2-fluoro-4-iodo-phenylamino)-benzoic acid 2-hydroxy-3-methyleneaminooxy-propyl ester; and pharmaceutically acceptable salts thereof, are provided herein.

In some aspects, the pharmaceutical composition comprises 3,4-Difluoro-2-(2-fluoro-4-iodo-phenylamino)-benzoic acid 2,3-dihydroxy-propyl ester. In some aspects, the pharmaceutical composition comprises 3,4-Difluoro-2-(2-fluoro-4-iodo-phenylamino)-benzoic acid 3-[1-carboxy-meth-(E)-ylideneaminooxy]-2-hydroxy-propyl ester. In some aspects, the pharmaceutical composition comprises 3,4-Difluoro-2-(2-fluoro-4-iodo-phenylamino)-benzoic acid 2-hydroxy-3-methyleneaminooxy-propyl ester.

Pharmaceutical compositions comprising a compound which is

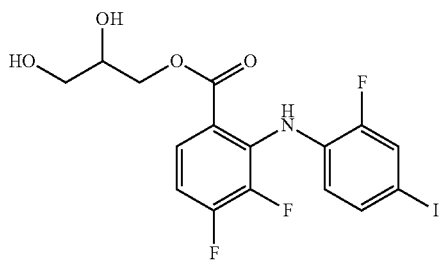 [SMILES: O=C(OCC(O)CO)c1ccc(F)c(F)c1Nc1ccc(I)cc1F]

or a pharmaceutically acceptable salt thereof are provided herein.

In some aspects, the compound is present in an amount of about 1 μg to about 10 mg, about 1 μg to about 9 mg, about 1 μg to about 8 mg, about 1 μg to about 7 mg, about 1 μg to about 6 mg, about 1 μg to about 5 mg, about 1 μg to about 4 mg, about 1 μg to about 3 mg, about 1 μg to about 2 mg, about 1 μg to about 1 mg, about 1 μg to about 950 μg, about 1 μg to about 900 μg, about 1 μg to about 850 μg, about 1 μg to about 800 μg, about 1 μg to about 750 μg, about 1 μg to about 700 μg, about 1 μg to about 650 μg, about 1 μg to about 600 μg, about 1 μg to about 550 μg, about 1 μg to about 500 μg, about 1 μg to about 450 μg, about 1 μg to about 400 μg, about 1 μg to about 350 μg, about 1 μg to about 300 μg, about 1 μg to about 250 μg, about 1 μg to about 200 μg, about 1 μg to about 150 μg, about 1 μg to about 100 μg, about 1 μg to about 75 μg, about 1 μg to about 50 μg, about 1 μg to about 25 μg, about 1 μg to about 20 μg, about 1 μg to about 15 μg, about 1 μg to about 10 μg, or about 1 μg to about 5 μg. In some aspects, the compound is present in an amount of about 10 mg, about 9.5 mg, about 9 mg, about 8.5 mg, about 8 mg, about 7.5 mg, about 7 mg, about 6.5 mg, about 6 mg, about 5.5 mg, about 5 mg, about 4.5 mg, about 4 mg, about 3.5 mg, about 3 mg, about 2.5 mg, about 2 mg, about 1.5 mg, about 1 mg, about 950 μg, about 900 μg, about 850 μg, about 800 μg, about 750 μg, about 700 μg, about 650 μg, about 600 μg, about 550 μg, about 500 μg, about 450 μg, about 400 μg, about 350 μg, about 300 μg, about 250 μg, about 200 μg, about 150 μg, about 100 μg, about 75 μg, about 50 μg, about 25 μg, about 20 μg, about 15 μg, about 10 μg, about 5 μg, or about 1 μg.

In some aspects, the pharmaceutical composition further comprises a MEK inhibitor selected from the group consisting of mirdametinib, binimetinib, cobimetinib, trametinib, and selumetinib, or a pharmaceutically acceptable salt thereof. In some aspects, the pharmaceutical composition further comprises mirdametinib, or a pharmaceutically acceptable salt thereof. In some aspects, the pharmaceutical composition further comprises binimetinib, or a pharmaceutically acceptable salt thereof In some aspects, the pharmaceutical composition further comprises cobimetinib, or a pharmaceutically acceptable salt thereof. In some aspects, the pharmaceutical composition further comprises trametinib, or a pharmaceutically acceptable salt thereof. In some aspects, the pharmaceutical composition further comprises selumetinib, or a pharmaceutically acceptable salt thereof.

In some aspects, the pharmaceutical composition further comprises a MEK inhibitor selected from the group consisting of mirdametinib, binimetinib, cobimetinib, trametinib, and selumetinib. In some aspects, the pharmaceutical composition further comprises mirdametinib. In some aspects, the pharmaceutical composition further comprises binimetinib. In some aspects, the pharmaceutical composition further comprises cobimetinib. In some aspects, the pharmaceutical composition further comprises trametinib. In some aspects, the pharmaceutical composition further comprises selumetinib.

In some aspects, the pharmaceutical composition further comprises mirdametinib, or a pharmaceutically acceptable salt thereof. In some aspects, the pharmaceutical composition comprises mirdametinib.

In some aspects, the pharmaceutical composition further comprises binimetinib, or a pharmaceutically acceptable salt thereof. In some aspects, the pharmaceutical composition further comprises binimetinib.

In some aspects, the pharmaceutical composition further comprises cobimetinib, or a pharmaceutically acceptable salt thereof. In some aspects, the pharmaceutical composition further comprises cobimetinib fumarate. In some aspects, the pharmaceutical composition further comprises cobimetinib.

In some aspects, the pharmaceutical composition further comprises trametinib, or a pharmaceutically acceptable salt thereof. In some aspects, the pharmaceutical composition comprises trametinib dimethyl sulfoxide. In some aspects, the pharmaceutical composition further comprises trametinib.

In some aspects, the pharmaceutical composition further comprises selumetinib, or a pharmaceutically acceptable salt thereof. In some aspects, the pharmaceutical composition further comprises selumetinib sulfate. In some aspects, the pharmaceutical composition further comprises selumetinib.

Pharmaceutical compositions comprising a compound which is

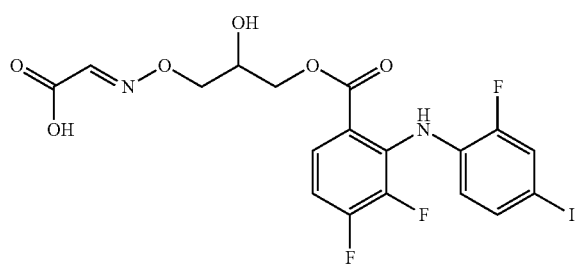 [SMILES: O=C(O)/C=N/OCC(O)COC(=O)c1ccc(F)c(F)c1Nc1ccc(I)cc1F]

or a pharmaceutically acceptable salt thereof are provided herein.

In some aspects, the compound is present in an amount of about 1 µg to about 10 mg, about 1 µg to about 9 mg, about 1 µg to about 8 mg, about 1 µg to about 7 mg, about 1 µg to about 6 mg, about 1 µg to about 5 mg, about 1 mg to about 4 mg, about 1 mg to about 3 mg, about 1 µg to about 2 mg, about 1 µg to about 1 mg, about 1 mg to about 950 mg, about 1 µg to about 900 µg, about 1 mg to about 850 mg, about 1 µg to about 800 µg, about 1 µg to about 750 µg, about 1 µg to about 700 µg, about 1 µg to about 650 µg, about 1 µg to about 600 µg, about 1 µg to about 550 µg, about 1 µg to about 500 µg, about 1 µg to about 450 µg, about 1 µg to about 400 µg, about 1µg to about 350 µg, about 1 µg to about 300 µg, about 1 µg to about 250 µg, about 1 µg to about 200 µg, about 1 µg to about 150 µg, about 1 µg to about 100 µg, about 1 µg to about 75 µg, about 1 µg to about 50 µg, about 1 µg to about 25 µg, about 1 µg to about 20 µg, about 1 µg to about 15 µg, about 1 µg to about 10 µg, or about 1 µg to about 5 µg. In some aspects, the compound is present in an amount of about 10 mg, about 9.5 mg, about 9 mg, about 8.5 mg, about 8 mg, about 7.5 mg, about 7 mg, about 6.5 mg, about 6 mg, about 5.5 mg, about 5 mg, about 4.5 mg, about 4 mg, about 3.5 mg, about 3 mg, about 2.5 µg, about 2 mg, about 1.5 mg, about 1 mg, about 950 µg, about 900 µg, about 850 µg, about 800 µg, about 750 µg, about 700 µg, about 650 µg, about 600 µg, about 550 µg, about 500 µg, about 450 µg, about 400 µg, about 350 µg, about 300 µg, about 250 µg, about 200 µg, about 150 µg, about 100 µg, about 75 µg, about 50 µg, about 25 µg, about 20 µg, about 15 µg, about 10 µg, about 5 µg, or about 1 µg.

In some aspects, the pharmaceutical composition further comprises a MEK inhibitor selected from the group consisting of mirdametinib, binimetinib, cobimetinib, trametinib, and selumetinib, or a pharmaceutically acceptable salt thereof. In some aspects, the pharmaceutical composition further comprises mirdametinib, or a pharmaceutically acceptable salt thereof. In some aspects, the pharmaceutical composition further comprises binimetinib, or a pharmaceutically acceptable salt thereof. In some aspects, the pharmaceutical composition further comprises cobimetinib, or a pharmaceutically acceptable salt thereof. In some aspects, the pharmaceutical composition further comprises trametinib, or a pharmaceutically acceptable salt thereof. In some aspects, the pharmaceutical composition further comprises selumetinib, or a pharmaceutically acceptable salt thereof.

In some aspects, the pharmaceutical composition further comprises a MEK inhibitor selected from the group consisting of mirdametinib, binimetinib, cobimetinib, trametinib, and selumetinib. In some aspects, the pharmaceutical composition further comprises mirdametinib. In some aspects, the pharmaceutical composition further comprises binimetinib. In some aspects, the pharmaceutical composition further comprises cobimetinib. In some aspects, the pharmaceutical composition further comprises trametinib. In some aspects, the pharmaceutical composition further comprises selumetinib.

In some aspects, the pharmaceutical composition further comprises mirdametinib, or a pharmaceutically acceptable salt thereof. In some aspects, the pharmaceutical composition comprises mirdametinib.

In some aspects, the pharmaceutical composition further comprises binimetinib, or a pharmaceutically acceptable salt thereof. In some aspects, the pharmaceutical composition further comprises binimetinib.

In some aspects, the pharmaceutical composition further comprises cobimetinib, or a pharmaceutically acceptable salt thereof. In some aspects, the pharmaceutical composition further comprises cobimetinib fumarate. In some aspects, the pharmaceutical composition further comprises cobimetinib.

In some aspects, the pharmaceutical composition further comprises trametinib, or a pharmaceutically acceptable salt thereof. In some aspects, the pharmaceutical composition comprises trametinib dimethyl sulfoxide. In some aspects, the pharmaceutical composition further comprises trametinib.

In some aspects, the pharmaceutical composition further comprises selumetinib, or a pharmaceutically acceptable salt thereof. In some aspects, the pharmaceutical composition further comprises selumetinib sulfate. In some aspects, the pharmaceutical composition further comprises selumetinib.

Pharmaceutical compositions comprising a compound which is

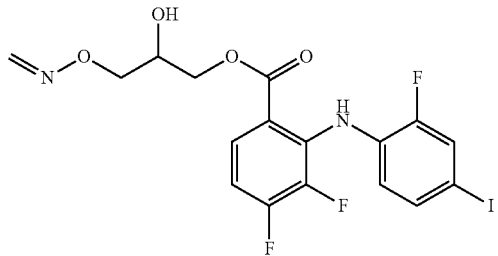 [SMILES: C=NOCC(O)COC(=O)c1ccc(F)c(F)c1Nc1ccc(I)cc1F]

or a pharmaceutically acceptable salt thereof are provided herein.

In some aspects, the compound is present in an amount of about 1 µg to about 10 mg, about 1 µg to about 9 mg, about 1 µg to about 8 mg, about 1 µg to about 7 mg, about 1 µg to about 6 mg, about 1 µg to about 5 mg, about 1 µg to about 4 mg, about 1 µg to about 3 mg, about 1 µg to about 2 mg, about 1 µg to about 1 mg, about 1 µg to about 950 µg, about 1 µg to about 900 µg, about 1 µg to about 850 µg, about 1 µg to about 800 µg, about 1 µg to about 750 µg, about 1 µg to about 700 µg, about 1 µg to about 650 µg, about 1 µg to about 600 µg, about 1 µg to about 550 µg, about 1 µg to about 500 µg, about 1 µg to about 450 µg, about 1 µg to about 400 µg, about 1 µg to about 350 µg, about 1 µg to about 300 µg, about 1 µg to about 250 µg, about 1 µg to about 200 µg, about 1 µg to about 150 µg, about 1 µg to about 100 µg, about 1 µg to about 75 µg, about 1 µg to about 50 µg, about 1 µg to about 25 µg, about 1 µg to about 20 µg, about 1 µg to about 15 µg, about 1 µg to about 10 µg, or about 1 µg to about 5 µg. In some aspects, the compound is present in an amount of about 10 mg, about 9.5 mg, about 9 mg, about 8.5 mg, about 8 mg, about 7.5 mg, about 7 mg, about 6.5 mg, about 6 mg, about 5.5 mg, about 5 mg, about 4.5 mg, about 4 mg, about 3.5 mg, about 3 mg, about 2.5 mg, about 2 mg, about 1.5 mg, about 1 mg, about 950 µg, about 900 µg, about 850 µg, about 800 µg, about 750 µg, about 700 µg, about 650 µg, about 600 µg, about 550 µg, about 500 µg, about 450 µg, about 400 µg, about 350 µg, about 300 µg, about 250 µg, about 200 µg, about 150 µg, about 100 µg, about 75 µg, about 50 µg, about 25 µg, about 20 µg, about 15 µg, about 10 µg, about 5 µg, or about 1 µg.

In some aspects, the pharmaceutical composition further comprises a MEK inhibitor selected from the group consisting of mirdametinib, binimetinib, cobimetinib, trametinib, and selumetinib, or a pharmaceutically acceptable salt thereof. In some aspects, the pharmaceutical composition further comprises mirdametinib, or a pharmaceutically acceptable salt thereof. In some aspects, the pharmaceutical composition further comprises binimetinib, or a pharmaceutically acceptable salt thereof. In some aspects, the pharmaceutical composition further comprises cobimetinib, or a pharmaceutically acceptable salt thereof. In some aspects, the pharmaceutical composition further comprises trametinib, or a pharmaceutically acceptable salt thereof. In some aspects, the pharmaceutical composition further comprises selumetinib, or a pharmaceutically acceptable salt thereof.

In some aspects, the pharmaceutical composition further comprises a MEK inhibitor selected from the group consisting of mirdametinib, binimetinib, cobimetinib, trametinib, and selumetinib. In some aspects, the pharmaceutical composition further comprises mirdametinib. In some aspects, the pharmaceutical composition further comprises binimetinib. In some aspects, the pharmaceutical composition further comprises cobimetinib. In some aspects, the pharmaceutical composition further comprises trametinib. In some aspects, the pharmaceutical composition further comprises selumetinib.

In some aspects, the pharmaceutical composition further comprises mirdametinib, or a pharmaceutically acceptable salt thereof. In some aspects, the pharmaceutical composition comprises mirdametinib.

In some aspects, the pharmaceutical composition further comprises binimetinib, or a pharmaceutically acceptable salt thereof. In some aspects, the pharmaceutical composition further comprises binimetinib.

In some aspects, the pharmaceutical composition further comprises cobimetinib, or a pharmaceutically acceptable salt thereof. In some aspects, the pharmaceutical composition further comprises cobimetinib fumarate. In some aspects, the pharmaceutical composition further comprises cobimetinib.

In some aspects, the pharmaceutical composition further comprises trametinib, or a pharmaceutically acceptable salt thereof. In some aspects, the pharmaceutical composition comprises trametinib dimethyl sulfoxide. In some aspects, the pharmaceutical composition further comprises trametinib.

In some aspects, the pharmaceutical composition further comprises selumetinib, or a pharmaceutically acceptable salt thereof. In some aspects, the pharmaceutical composition further comprises selumetinib sulfate. In some aspects, the pharmaceutical composition further comprises selumetinib.

III. Methods of Treatment

Methods for treating one or more tumor or cancer selected from the group consisting of plexiform neurofibromas (PN), plexiform neurofibromas associated with neurofibromatosis type 1 (NF1-PN), cutaneous neurofibromas (cNF), high grade glioma (HGG), low grade ovarian cancer, tuberous sclerosis (TSC), pancreatic ductal adenocarcinoma (PDAC), Langerhans cell histiocytosis (LCH), brain cancer, and a cancer that has metastasized to a patient's brain, comprises administering (e.g., orally) to a patient in need thereof a pharmaceutical composition provided above. In one embodiment, the method comprises administering (e.g., orally) an effective amount of one or more pharmaceutical compositions as described herein.

In some aspects, the tumor or cancer is plexiform neurofibromas (PN).

In some aspects, the tumor or cancer is plexiform neurofibromas associated with neurofibromatosis type 1 (NF1-PN).

In some aspects, the tumor or cancer is cutaneous neurofibromas (cNF).

In some aspects, the tumor or cancer is high grade glioma (HGG).

In some aspects, the tumor or cancer is low grade ovarian cancer.

In some aspects, the tumor or cancer is tuberous sclerosis (TSC).

In some aspects, the tumor or cancer is pancreatic ductal adenocarcinoma (PDAC).

In some aspects, the tumor or cancer is Langerhans cell histiocytosis (LCH).

In some aspects, the tumor or cancer is brain cancer.

In some aspects, the tumor or cancer is a cancer that has metastasized to a patient's brain.

EXAMPLE

Example 1: Synthesis of 3,4-Difluoro-2-(2-fluoro-4-iodo-phenylamino)-benzoic acid 2,3-dihydroxy-propyl ester

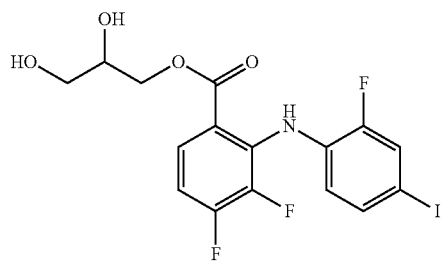 [SMILES: O=C(OCC(O)CO)c1ccc(F)c(F)c1Nc1ccc(I)cc1F]

The synthesis of 3,4-Difluoro-2-(2-fluoro-4-iodo-phenylamino)-benzoic acid 2,3-dihydroxy-propyl ester was carried out based on Scheme 1 provided below. Starting with the fluorinated phenyl amino acid and reacting with solketol (1A) provided the primary alcohol ester of the glycerol with the acid. Since there is only one free hydroxyl group the esterification can happen only through that hydroxyl group to provide compound 2A. The acetonide deprotection using acidic DOWEX resin resulted the desired compound, 3,4-Difluoro-2-(2-fluoro-4-iodo-phenylamino)-benzoic acid 2,3-dihydroxy-propyl ester. The structure of the compound was confirmed with NMR that showed characteristic peaks from the methylene protons of the ester at chemical shifts of 4.4 ppm. The methine proton on the secondary carbon is observed as a multiplet at 4.05 ppm and the methylene protons on the alcohol are observed as two doublets at 3.8 and 3.65 ppm.

Scheme 1: Synthesis of 3,4-Difluoro-2-(2-fluoro-4-iodo-phenylamino)-benzoic acid 2,3-dihydroxy-propyl ester

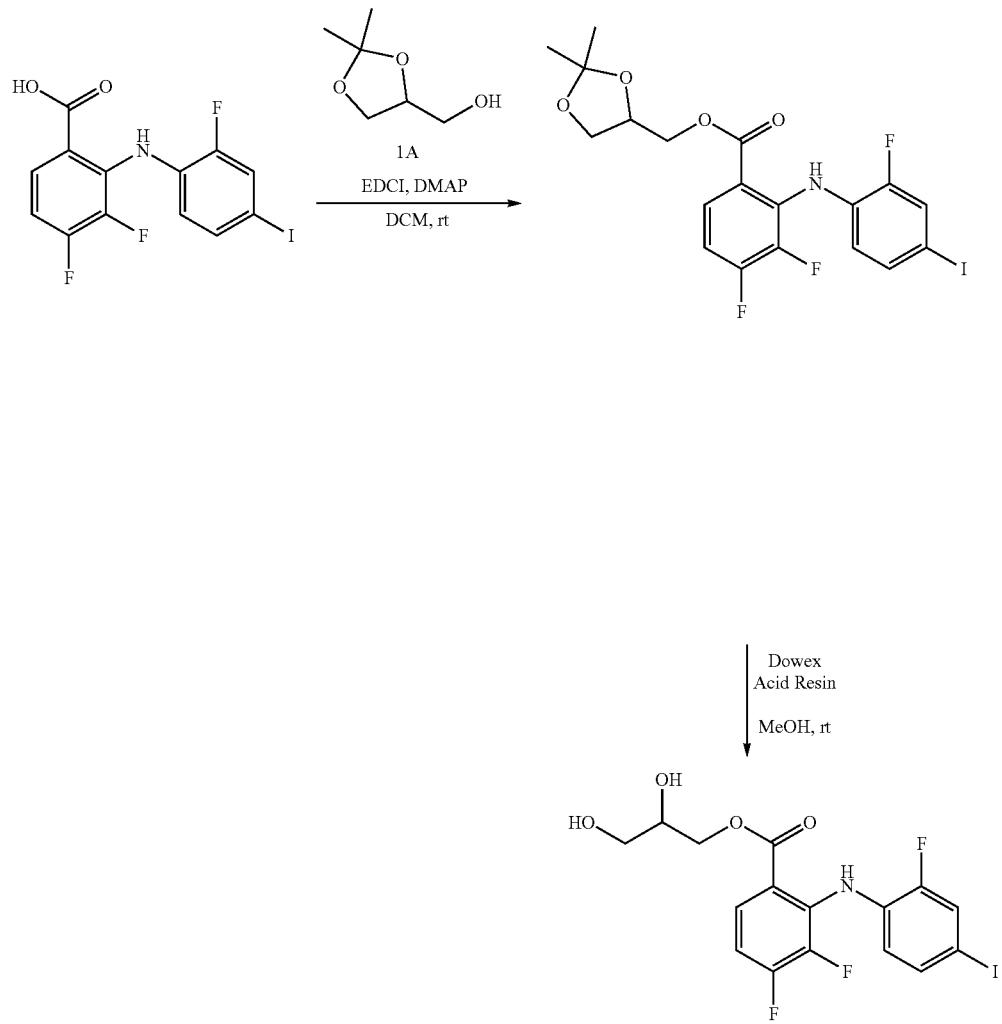

Example 2: Synthesis of 3,4-Difluoro-2-(2-fluoro-4-iodo-phenylamino)-benzoic acid 2-hydroxy-3-methyleneaminooxy-propyl ester

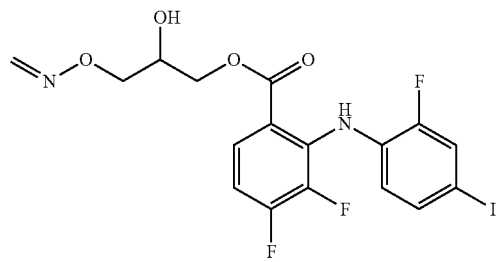 [SMILES: C=NOCC(O)COC(=O)c1ccc(F)c(F)c1Nc1ccc(I)cc1F]

The synthesis of 3,4-Difluoro-2-(2-fluoro-4-iodo-phenylamino)-benzoic acid 2-hydroxy-3-methyleneaminooxy-propyl ester was carried out based on Scheme 2 provided below. Deprotection of the acetonide group of the starting material used Dowex acid resin in methanol to provide the diol (1). The diol intermediate was purified by column chromatography before proceeding to the next stage. The coupling reaction of the diol with the acid provided compound 2. Deprotection of compound 2 was completed in toluene with ammonium hydroxide at 40° C.

The progress of the reaction was monitored by LCMS, which indicated a very clean reaction resulted compound 3 in high yield. This product was also characterized by 1H NMR to ensure that the ester bond is formed through the primary alcohol. Compound 3 is highly reactive and readily forms a Schiff's base with aldehydes and ketones. Reaction of formaldehyde (36% solution in water) with compound 3 in THF, in the presence of catalytic acetic acid resulted in the formation of the desired compound, 3,4-Difluoro-2-(2-fluoro-4-iodo-phenylamino)-benzoic acid 2-hydroxy-3-methyleneaminooxy-propyl ester.

Scheme 2: Synthesis of 3,4-Difluoro-2-(2-fluoro-4-iodo-phenylamino)-benzoic acid 2-hydroxy-3- methyleneaminooxy-propyl ester

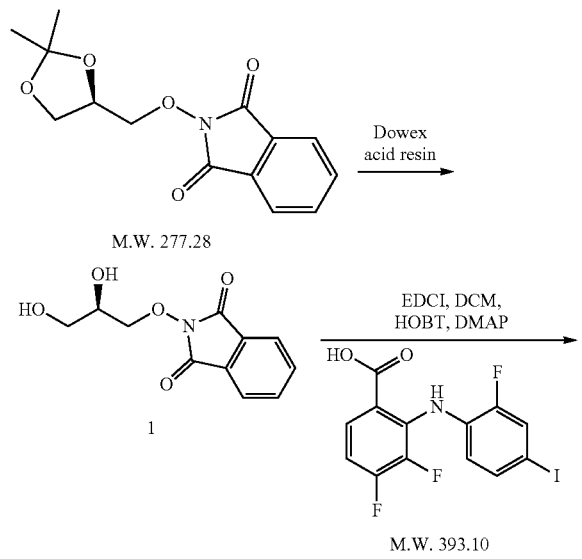

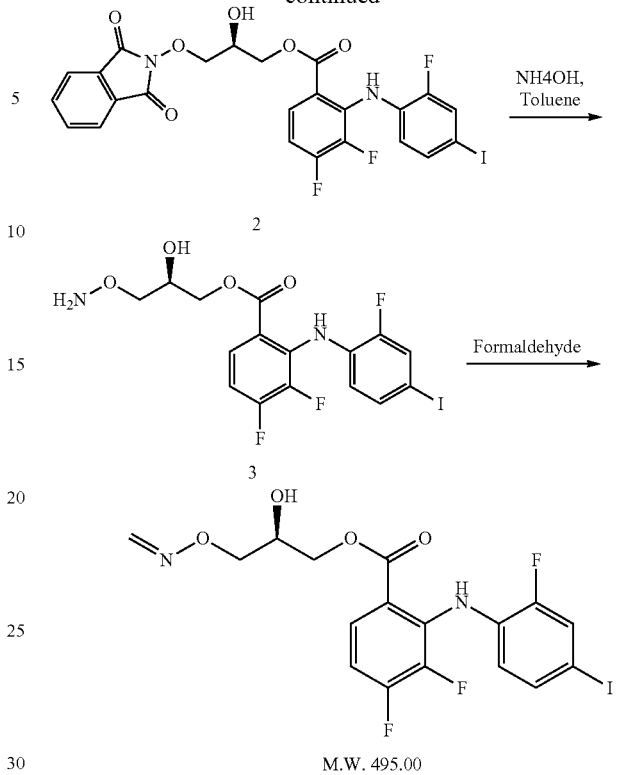

M.W. 495.00

Example 3: Synthesis of 3,4-Difluoro-2-(2-fluoro-4-iodo-phenylamino)-benzoic acid 3-[1-carboxy-meth-(E)-ylideneaminooxy]-2-hydroxy-propyl ester

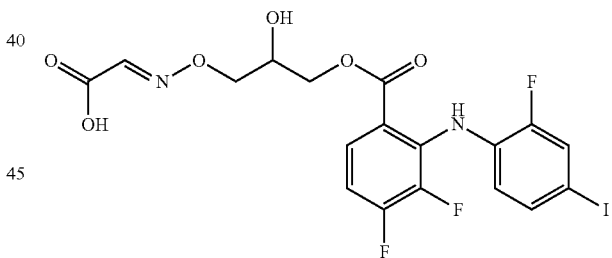

The synthesis of 3,4-Difluoro-2-(2-fluoro-4-iodo-phenylamino)-benzoic acid 3-[1-carboxy-meth-(E)-ylideneaminooxy]-2-hydroxy-propyl ester was carried out based on Scheme 3 provided below. The synthesis of 3,4-Difluoro-2-(2-fluoro-4-iodo-phenylamino)-benzoic acid 3-[1-carboxy-meth-(E)-ylideneaminooxy]-2-hydroxy-propyl ester followed the same process as 3,4-Difluoro-2-(2-fluoro-4-iodo-phenylamino)-benzoic acid 2-hydroxy-3-methyleneaminooxy-propyl ester. The reaction of compound 3 with glyoxylic acid, in the presence of trace amounts of acetic acid produced 3,4-Difluoro-2-(2-fluoro-4-iodo-phenylamino)-benzoic acid 3-[1-carboxy-meth-(E)-ylideneaminooxy]-2-hydroxy-propyl ester.

Using column purification and crystallization in a mixture of 10% EtOAc in heptane, 3,4-Difluoro-2-(2-fluoro-4-iodo-phenylamino)-benzoic acid 3-[1-carboxy-meth-(E)-ylideneaminooxy]-2-hydroxy-propyl ester was obtained in >95% purity.

Scheme 3: Synthesis of 3,4-Difluoro-2-(2-fluoro-ido-phenylamino)-benzoic acid 3-[1-carboxy-meth-(E)-ylideneaminooxy]-2-hydroxy-propyl ester

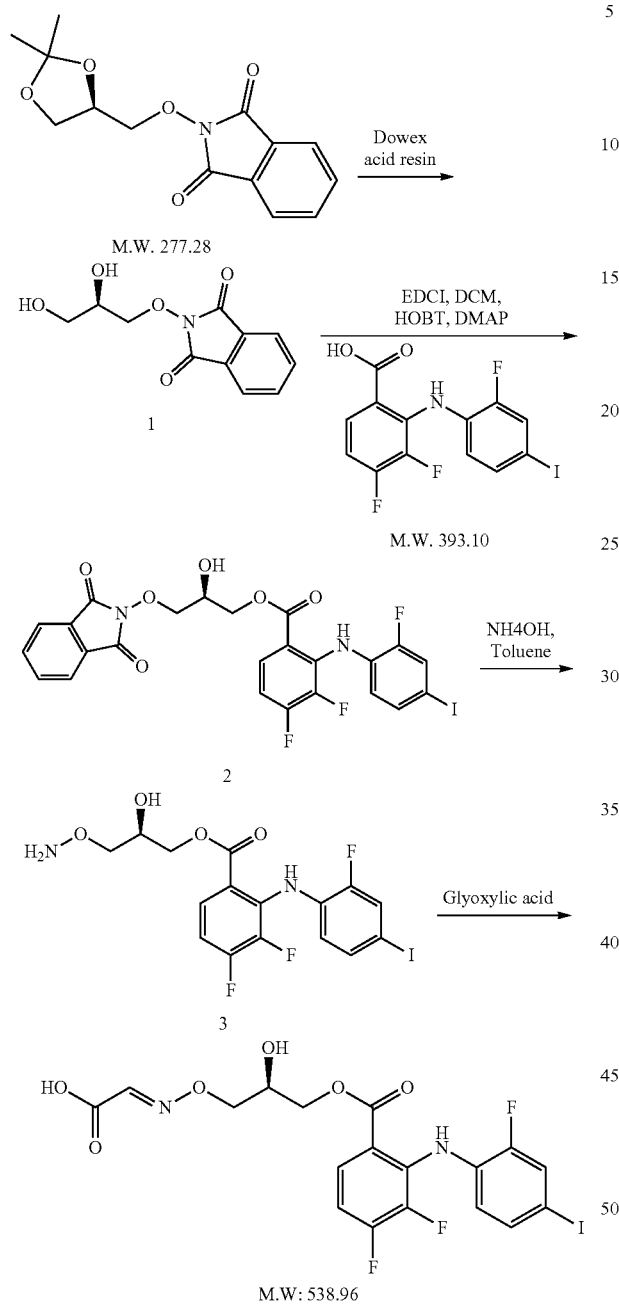

cation is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

In addition to the various embodiments described herein, the present disclosure includes the following embodiments numbered E1 through E39. This list of embodiments is presented as an exemplary list and the application is not limited to these embodiments.

E1. A compound which is

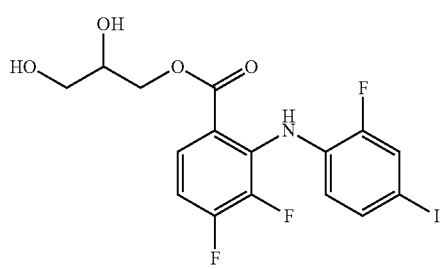 [SMILES: O=C(OCC(O)CO)c1ccc(F)c(F)c1Nc1ccc(I)cc1F]

or a pharmaceutically acceptable salt thereof.

E2. A compound which is

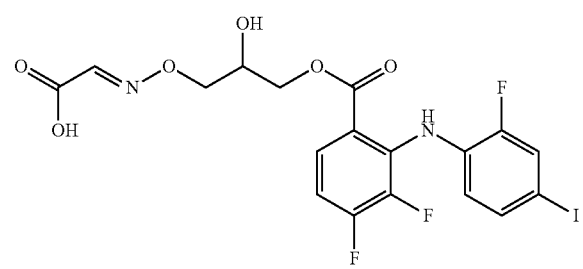 [SMILES: O=C(O)/C=N/OCC(O)COC(=O)c1ccc(F)c(F)c1Nc1ccc(I)cc1F]

or a pharmaceutically acceptable salt thereof.

E3. A compound which is

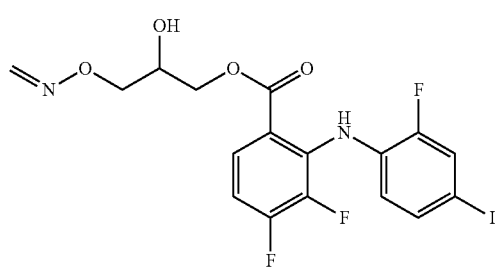 [SMILES: C=NOCC(O)COC(=O)c1ccc(F)c(F)c1Nc1ccc(I)cc1F]

or a pharmaceutically acceptable salt thereof.

E4. A pharmaceutical composition comprising a compound selected from the group consisting of: 3,4-Difluoro-2-(2-fluoro-4-iodo-phenylamino)-benzoic acid 2,3-dihydroxy-propyl ester; 3,4-Difluoro-2-(2-fluoro-4-iodo-phenylamino)-benzoic acid 3-[1-carboxy-meth-(E)-ylideneaminooxy]-2-hydroxy-propyl ester; 3,4-Difluoro-2-(2-fluoro-4-iodo-phenylamino)-benzoic acid 2-hydroxy-3-methyleneaminooxy-propyl ester; and pharmaceutically acceptable salts thereof.

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this appli- E5. A pharmaceutical composition comprising a compound which is

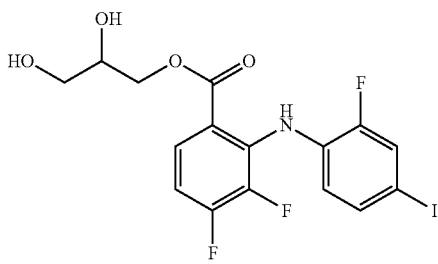 [SMILES: O=C(OCC(O)CO)c1ccc(F)c(F)c1Nc1ccc(I)cc1F]

or a pharmaceutically acceptable salt thereof.

E6. The pharmaceutical composition according to E5 wherein the compound is present in an amount of about 1 μg to about 10 mg.

E7. The pharmaceutical composition according to E5 wherein the compound is present in an amount of about 1 μg to about 8 mg.

E8. The pharmaceutical composition according to E5 wherein the compound is present in an amount of about 1 μg to about 1 mg.

E9. The pharmaceutical composition according to E5 wherein the compound is present in an amount of about 1 μg to about 500 μg.

E10. The pharmaceutical composition according to E5 wherein the compound is present in an amount of about 1 μg to about 250 μg.

E11. The pharmaceutical composition according to E5 wherein the compound is present in an amount of about 1 μg to about 100 μg.

E12. The pharmaceutical composition according to E5 wherein the compound is present in an amount of about 1 μg to about 50 μg.

E13. The pharmaceutical composition according to E5 wherein the compound is present in an amount of about 1 μg to about 25 μg.

E14. The pharmaceutical composition according to E5 wherein the compound is present in an amount of about 1 μg to about 10 μg.

E15. The pharmaceutical composition according to any one of E5-E14 further comprising a MEK inhibitor selected from the group consisting of mirdametinib, binimetinib, cobimetinib, trametinib, and selumetinib, or a pharmaceutically acceptable salt thereof.

E16. The pharmaceutical composition according to any one of E5-E14 further comprising mirdametinib.

E17. A pharmaceutical composition comprising a compound which is

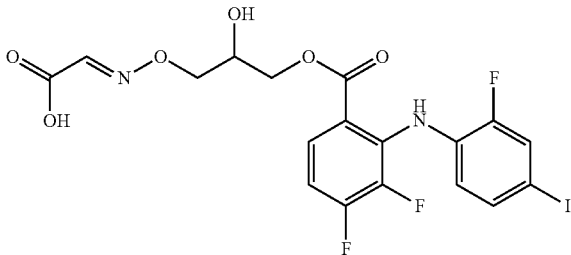 [SMILES: O=C(O)/C=N/OCC(O)COC(=O)c1ccc(F)c(F)c1Nc1ccc(I)cc1F]

or a pharmaceutically acceptable salt thereof.

E18. The pharmaceutical composition according to E17 wherein the compound is present in an amount of about 1 μg to about 10 mg.

E19. The pharmaceutical composition according to E17 wherein the compound is present in an amount of about 1 μg to about 8 mg.

E20. The pharmaceutical composition according to E17 wherein the compound is present in an amount of about 1 μg to about 1 mg.

E21. The pharmaceutical composition according to E17 wherein the compound is present in an amount of about 1 μg to about 500 μg.

E22. The pharmaceutical composition according to E17 wherein the compound is present in an amount of about 1 μg to about 250 μg.

E23. The pharmaceutical composition according to E17 wherein the compound is present in an amount of about 1 μg to about 100 μg.

E24. The pharmaceutical composition according to E17 wherein the compound is present in an amount of about 1 μg to about 50 μg.

E25. The pharmaceutical composition according to E17 wherein the compound is present in an amount of about 1 μg to about 10 μg.

E26. The pharmaceutical composition according to any one of E17-E25 further comprising a MEK inhibitor selected from the group consisting of mirdametinib, binimetinib, cobimetinib, trametinib, and selumetinib, or a pharmaceutically acceptable salt thereof.

E27. The pharmaceutical composition according to any one of E17-E25 further comprising mirdametinib.

E28. A pharmaceutical composition comprising a compound which is

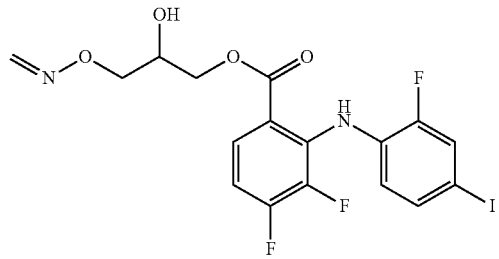 [SMILES: C=NOCC(O)COC(=O)c1ccc(F)c(F)c1Nc1ccc(I)cc1F]

or a pharmaceutically acceptable salt thereof.

E29. The pharmaceutical composition according to E28 wherein the compound is present in an amount of about 1 μg to about 10 mg.

E30. The pharmaceutical composition according to E28 wherein the compound is present in an amount of about 1 μg to about 8 mg.

E31. The pharmaceutical composition according to E28 wherein the compound is present in an amount of about 1 μg to about 1 mg.

E32. The pharmaceutical composition according to E28 wherein the compound is present in an amount of about 1 μg to about 500 μg.

E33. The pharmaceutical composition according to E28 wherein the compound is present in an amount of about 1 μg to about 250 μg.

E34. The pharmaceutical composition according to E28 wherein the compound is present in an amount of about 1 μg to about 100 μg.

E35. The pharmaceutical composition according to E28 wherein the compound is present in an amount of about 1 µg to about 50 µg.

E36. The pharmaceutical composition according to E28 wherein the compound is present in an amount of about 1 µg to about 10 µg.

E37. The pharmaceutical composition according to any one of E28-E36 further comprising a MEK inhibitor selected from the group consisting of mirdametinib, binimetinib, cobimetinib, trametinib, and selumetinib, or a pharmaceutically acceptable salt thereof.

E38. The pharmaceutical composition according to any one of E28-E36 further comprising mirdametinib.

E39. A method for treating a tumor or cancer selected from the group consisting of plexiform neurofibromas (PN), plexiform neurofibromas associated with neurofibromatosis type 1 (NF1-PN), cutaneous neurofibromas (cNF), pancreatic ductal adenocarcinoma (PDAC), high grade glioma (HGG), low grade ovarian cancer, tuberous sclerosis (TSC), Langerhans cell histiocytosis (LCH), brain cancer, and a cancer that has metastasized to a patient's brain, comprising administering to a patient in need thereof a pharmaceutical composition according to any one of E4-E38.

What is claimed:

1. A compound which is selected from the group consisting of:

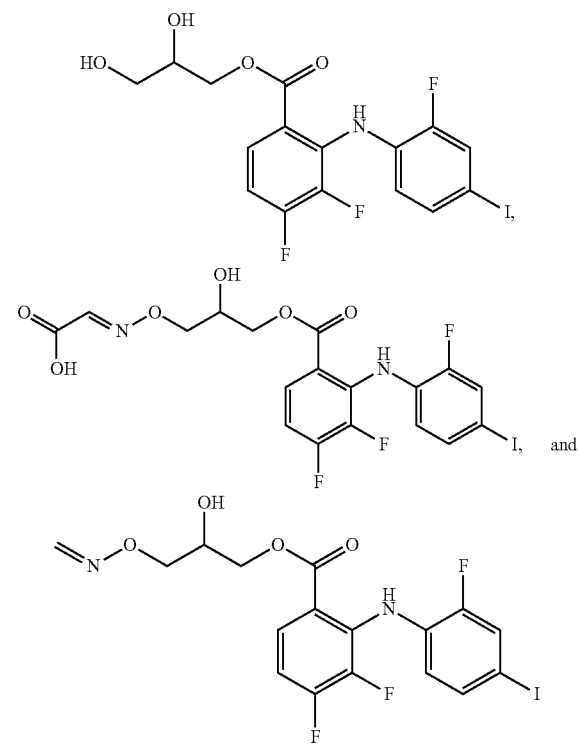

and pharmaceutically acceptable salts thereof.

2. A pharmaceutical composition comprising (a) a compound selected from the group consisting of:
   3,4-Difluoro-2-(2-fluoro-4-iodo-phenylamino)-benzoic acid 2,3-dihydroxy-propyl ester;
   3,4-Difluoro-2-(2-fluoro-4-iodo-phenylamino)-benzoic acid 3-[1-carboxy-meth-(E)-ylideneaminooxy]-2-hydroxy-propyl ester;
   3,4-Difluoro-2-(2-fluoro-4-iodo-phenylamino)-benzoic acid 2-hydroxy-3-methyleneaminooxy-propyl ester; and pharmaceutically acceptable salts thereof; and (b) a pharmaceutically acceptable carrier.

3. The pharmaceutical composition according to claim 2, wherein the composition comprises (a)

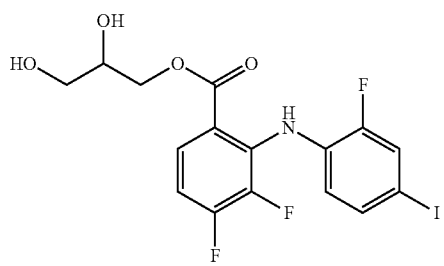 [SMILES: O=C(OCC(O)CO)c1ccc(F)c(F)c1Nc1ccc(I)cc1F]

or a pharmaceutically acceptable salt thereof.

4. The pharmaceutical composition according to claim 3 wherein the compound is present in an amount of about 1 µg to about 10 mg.

5. The pharmaceutical composition according to claim 3, further comprising a MEK inhibitor selected from the group consisting of mirdametinib, binimetinib, cobimetinib, trametinib, and selumetinib, or a pharmaceutically acceptable salt thereof.

6. The pharmaceutical composition according to claim 5, wherein the MEK inhibitor is mirdametinib.

7. The pharmaceutical composition according to claim 2, wherein the composition comprises (a)

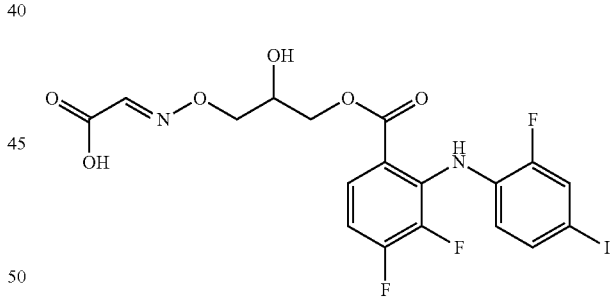

or a pharmaceutically acceptable salt thereof.

8. The pharmaceutical composition according to claim 7 wherein the compound is present in an amount of about 1 µg to about 10 mg.

9. The pharmaceutical composition according to claim 7, further comprising a MEK inhibitor selected from the group consisting of mirdametinib, binimetinib, cobimetinib, trametinib, and selumetinib, of a pharmaceutically acceptable salt thereof.

10. The pharmaceutical composition according to claim 9, wherein the MEK inhibitor is mirdametinib.

11. The pharmaceutical composition according to claim 2, wherein the composition comprises (a)

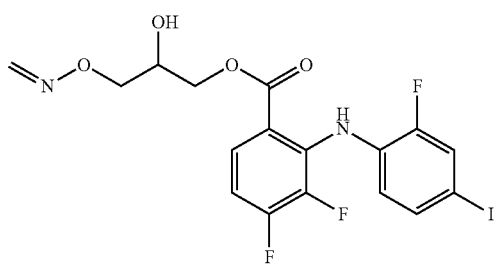 [SMILES: C=NOCC(O)COC(=O)c1ccc(F)c(F)c1Nc1ccc(I)cc1F]

or a pharmaceutically acceptable salt thereof.

12. The pharmaceutical composition according to claim 11 wherein the compound is present in an amount of about 1 µg to about 10 mg.

13. The pharmaceutical composition according to claim 11 further comprising a MEK inhibitor selected from the group consisting of mirdametinib, binimetinib, cobimetinib, trametinib, and selumetinib, or a pharmaceutically acceptable salt thereof.

14. The pharmaceutical composition according to claim 13, wherein the MEK inhibitor is mirdametinib.

15. A method for treating a tumor or cancer selected from the group consisting of plexiform neurofibromas (PN), plexiform neurofibromas associated with neurofibromatosis type 1 (NF1-PN), cutaneous neurofibromas (cNF), pancreatic ductal adenocarcinoma (PDAC), high grade glioma (HGG), low grade ovarian cancer, tuberous sclerosis (TSC), Langerhans cell histiocytosis (LCH), brain cancer, and a cancer that has metastasized to a patient's brain, comprising administering to a patient in need thereof a pharmaceutical composition according to claim 6.

16. A method for treating plexiform neurofibromas associated with neurofibromatosis type 1 (NF1-PN) in a patient in need thereof comprising administering to the patient a pharmaceutical composition of claim 6.

17. A method for treating plexiform neurofibromas associated with neurofibromatosis type 1 (NF1-PN) in a patient in need thereof comprising administering to the patient a pharmaceutical composition of claim 10.

18. A method for treating plexiform neurofibromas associated with neurofibromatosis type 1 (NF1-PN) in a patient in need thereof comprising administering to the patient a pharmaceutical composition of claim 14.

* * * * *